US00PP35441P2

(12) United States Plant Patent
Baird et al.

(10) Patent No.: US PP35,441 P2
(45) Date of Patent: Oct. 24, 2023

(54) BERMUDAGRASS NAMED 'UCR TP6-3'

(50) Latin Name: ***Cynodon dactylon* (L.) Persoon x. *Cynodon transvaalensis* Burtt-Davy.**
Varietal Denomination: UCR TP6-3

(71) Applicant: The Regents of the University of California, Oakland, CA (US)

(72) Inventors: James H. Baird, Rvierside, CA (US); Adam J. Lukaszewski, Riverside, CA (US); Marta Pudzianowska, Riverside, CA (US); Christian S. Bowman, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 31 days.

(21) Appl. No.: 17/803,475

(22) Filed: Jul. 27, 2022

(51) Int. Cl.
*A01H 5/12* (2018.01)
*A01H 6/00* (2018.01)

(52) U.S. Cl.
USPC ..... Plt./389

(58) Field of Classification Search
USPC ..... Plt./389
See application file for complete search history.

(56) References Cited

U.S. PATENT DOCUMENTS

| | | | |
|---|---|---|---|
| PP11,181 | P | 1/2000 | Riley |
| PP24,271 | P3 | 2/2014 | Wu et al. |
| PP27,392 | P2 | 11/2016 | Hanna et al. |
| PP31,695 | P3 | 4/2020 | Wu et al. |

*Primary Examiner* — Susan McCormick Ewoldt
(74) *Attorney, Agent, or Firm* — McKee, Voorhees & Sease, PLC

(57) ABSTRACT

A clonally propagated triploid turfgrass cultivar with improved winter color retention, drought resistance, and turf quality characteristics is disclosed.

2 Drawing Sheets

Botanical designation:

Genus and species: *Cynodon dactylon* (L.) Persoon x. *Cynodon transvaalensis* Burtt-Davy.

Cultivar denomination: The new plant has the cultivar varietal denomination 'UCR TP6-3'.

BACKGROUND

Turfgrass offers many aesthetic, functional, and environmental benefits, especially in increasingly urbanized environments. However, declining water resources and extended drought are jeopardizing use of turfgrass in California and other arid regions. Warm-season or C4 turfgrass species including bermudagrass are much better adapted to heat, drought, and salinity compared to cool-season grasses, but they go dormant during winter months making them less desirable choices for lawns, athletic fields, and golf courses. Clear differences in winter color retention, drought tolerance, and water use efficiency exist among warm-season grasses, and even within individual species, indicating that genetic improvements are possible. Accordingly, there is a need for improved bermudagrass genotypes with emphasis on winter color retention and drought resistance for Mediterranean and arid climates.

BRIEF SUMMARY

This disclosure relates to a new and distinct cultivar of Bermudagrass designated 'UCR TP6-3' and botanically known as *Cynodon dactylon* (L.) Persoon x. *Cynodon transvaalensis* Burtt-Davy. 'UCR TP6-3' is a turf-type, clonally propagated, triploid bermudagrass hybrid characterized by medium-fine texture, dark blue-green color, and high quality suitable for golf course fairways.

Using conventional breeding techniques, applicants crossed bermudagrass species and planted the progeny (seed) in the greenhouse and later in the field for selection of desired traits. 'UCR TP6-3' has consistently demonstrated superior winter color retention, drought resistance, and especially aesthetic turf quality characteristics in repeated field trials across California and in other states. It is comparable or superior to commercially available cultivars for most turf quality characteristics. This cultivar will be useful for water savings in urban landscapes and is a step in the right direction toward eliminating the need to overseed bermudagrass in the winter months for green color.

DETAILED BOTANICAL DESCRIPTION

Figure 1:
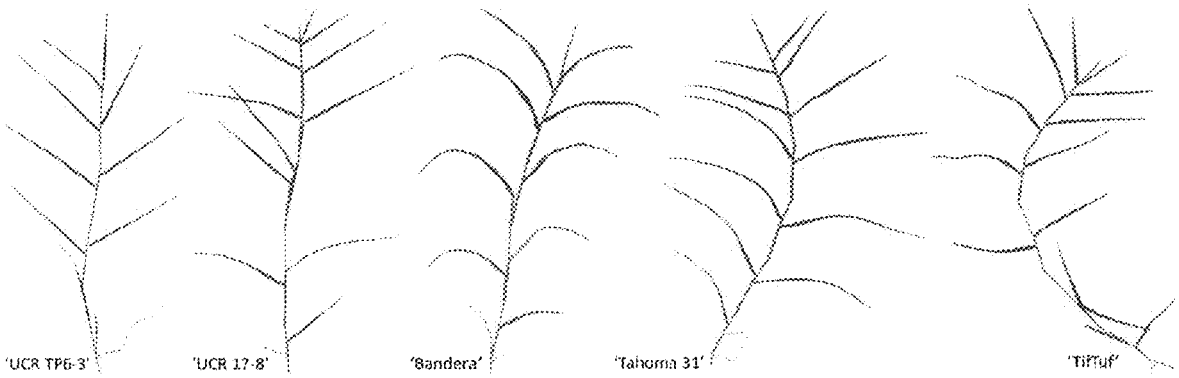
FIG. 1 is a photograph comparing shoots of 'UCR TP6-3', 'UCR 17-8', 'Bandera', 'Tahoma 31', and 'TifTuf', maintained in a greenhouse.
Figure 2:
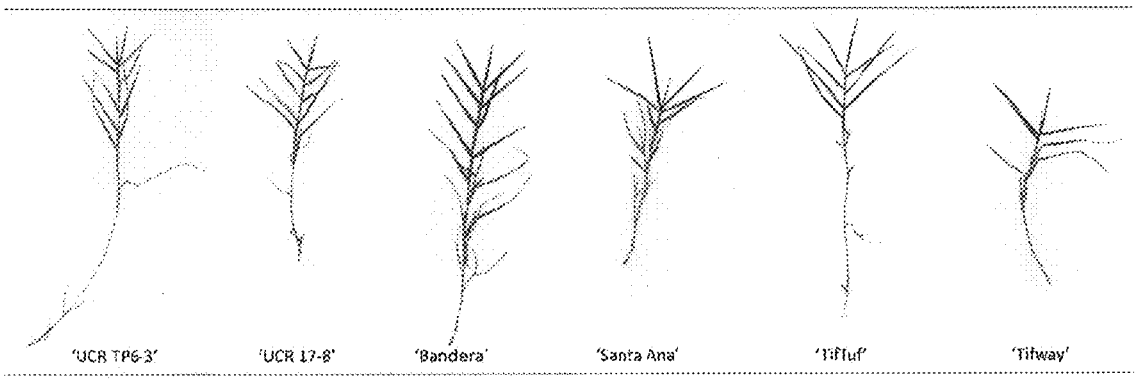
FIG. 2 is a photograph comparing shoots of 'UCR TP6-3', 'UCR 17-8', 'Bandera', 'Santa Ana', 'TifTuf' and 'Tifway', grown in the field.
Figure 3:
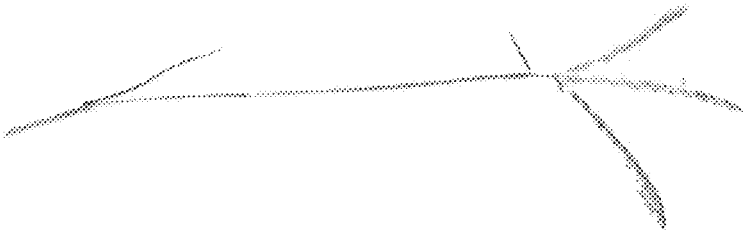
FIG. 3 is a photograph of an inflorescence of 'UCR TP6-3'.
Figure 4:
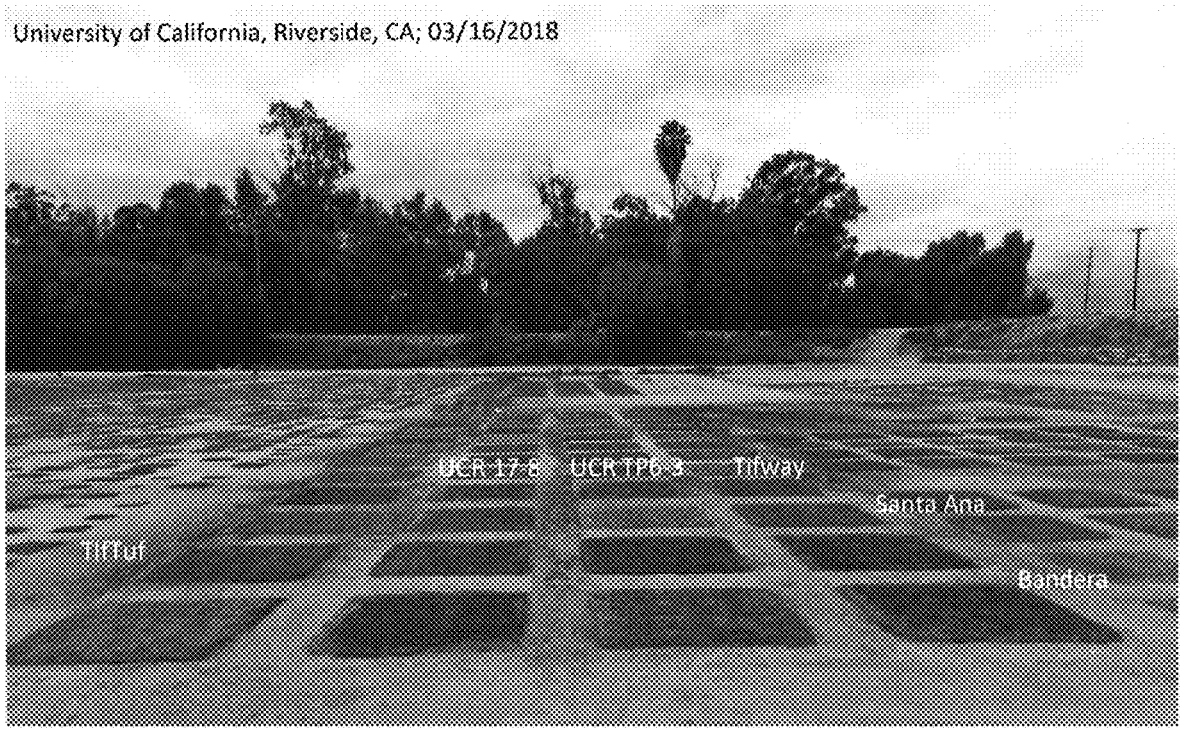
FIG. 4 is a photograph of plots of 'UCR TP6-3', 'UCR 17-8', 'Bandera', 'Santa Ana', 'TifTuf', and 'Tifway' in a replicated trial in Riverside, Calif. in March 2018.
Figure 5:
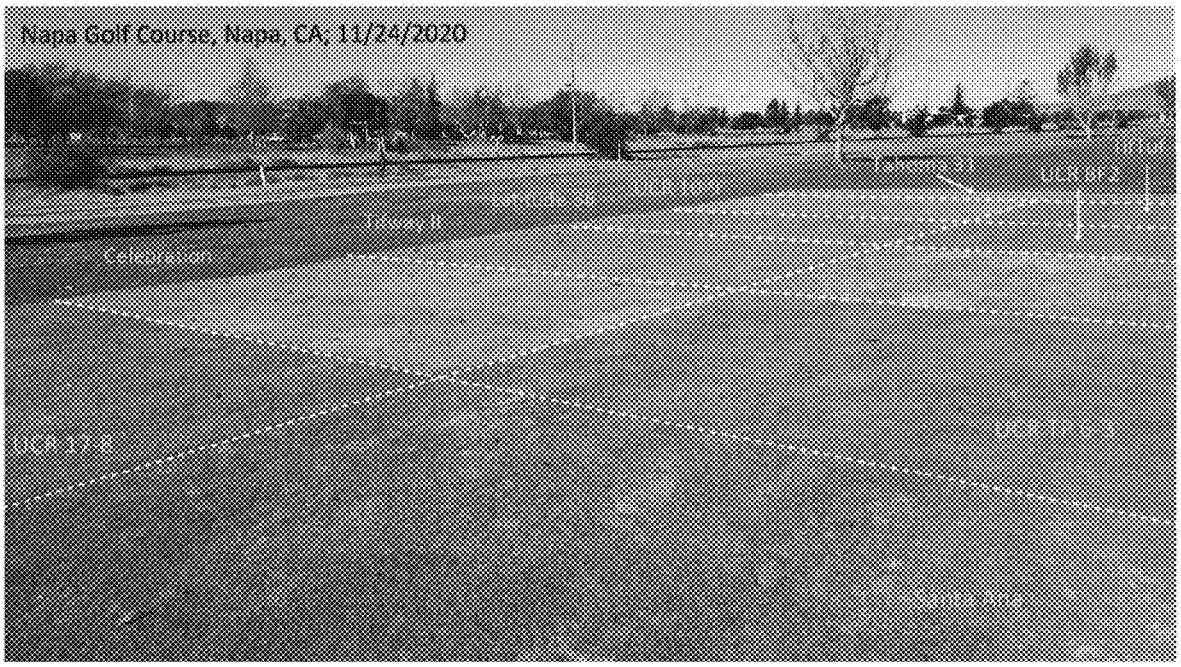
FIG. 5 is a photograph comparing fall color retention of 'UCR TP6-3', 'UCR 17-8', 'UCR BF2', 'UCR 10-9', 'Bandera', 'Celebration', 'Latitude 36', 'Santa Ana', 'TifTuf' 'Tahoma 31' and 'Tifway II' in Napa, CA in November 2020.

The following is a detailed botanical description of the new cultivar of Bermudagrass, its flowers, foliage etc. as based on two to three years of continuous observations of specimens grown in greenhouse and field conditions in various locations in California.

Origin and History

'UCR TP6-3' is a distinct cultivar resulting from a cross between diploid seed (female) parent *Cynodon transvaalensis* Burtt-Davy (Accession No. PI 290813) and tetraploid pollen (male) parent *Cynodon dactylon/transvaalensis* (Accession No. PI 647878). *Cynodon dactylon/transvaalensis* was initially identified as *Cynodon dactylon* and later re-identified as *Cynodon transvaalensis* in the GRIN database. Recent study of *Cynodon* spp. genetic diversity and population structure (Pudzianowska and Baird, 2020) indicate however that initial identification of PI647878 as *C. dactylon* is more probable, as it clustered together with other accessions identified as *C. dactylon*, and shows in its population composition two populations not found in most *C. transvaalensis* accessions. Crossing was achieved by detaching tillers and placing them in close proximity in a greenhouse, isolated from other bermudagrass plants. Resultant seeds were harvested in 2013 and planted in 2014 alongside 400 other hybrids in a screening nursery in Riverside, Calif. Thirty-six hybrids were selected for further evaluation in Riverside, Calif. in 2015 and in 2017 twelve were advanced for evaluation in a replicated trial in three different regions of California. In 2019, several trials were established in Riverside, Calif. and other California locations to further evaluate 'UCR TP6-3' and three other superior bermudagrass hybrids.

'UCR TP6-3' is sterile and must be propagated vegetatively. It has been clonally propagated in Riverside, Calif. through many seasons since 2014 and advanced generation clonal plants appear identical to the original plant in morphological phenotype and in genetic characteristics that have been measured.

Morphological Characteristics

'UCR TP6-3' forms a turf of medium-fine texture. The leaf blade is flat, sparsely hairy, with longer hair on the adaxial surface and shorter hair on the abaxial surface. The leaf blade tapers toward the tip. Short hairs are present on the leaf margin. Vernation is folded, leaf tip is pointed, ligule is a fringe of hair, collar is narrow and continuous, and auricles—absent. The color of the top and bottom surface of the leaf is dark green, with color space CIE Lab values for top surface L=8.45, a=−19.10, b=14.39, and for bottom surface L=8.72, a=−19.30, b=14.11 (values for top and bottom surface translate to RHS 135A, dark green, in The Royal Horticultural Society Colour Chart, 5$^{th}$ edition (2007)). The inflorescence is usually three spicate branches on a distinct culm of approximately 89 mm of length, and CIE Lab color of L=46.62, a=−13.38, b=19.64 (RHS 137C, medium brown green).

Morphological characteristics for mature plants of 'UCR TP6-3' grown in a greenhouse in Riverside, Calif. are found in Table 1 alongside 'UCR 17-8' (U.S. Plant patent application Ser. No. 17/803,476) and three commercial cultivars 'Bandera' (not patented), 'Tahoma 31' (experimental name 'OKC 1131', U.S. Plant Pat. No. 31,695), and 'TifTuf' (experimental name 'DT-1', U.S. Plant Pat. No. 27,392). Leaf blade width, leaf blade length, internode diameter, and internode length were measured on potted plants. Measurements were collected from three replications of each cultivar with 12 subsamples of each replication in 2019. 'UCR TP6-3's' leaf blade width was found to be similar to 'UCR 17-8', but narrower than that of 'Bandera', 'Tahoma 31', and 'Tiftuf'. 'UCR TP6-3's' leaf blade length was found to be longer than that of 'UCR 17-8', 'Bandera', 'Tahoma 31' and 'TifTuf'. Internode diameter of 'UCR TP6-3' was similar to that of 'UCR 17-8', and narrower than that of 'Bandera', 'Tahoma 31', and 'Tiftuf'.Internode length was similar to that of 'UCR 17-8' and 'Tiftuf', but longer than that of 'Bandera' and 'Tahoma 31'. The color of the internodes of 'UCR TP6-3' in CIE Lab color space is L=48.81, a=−14.57, b=20.87 (RHS 138A, medium brown green).

TABLE 1

Stolon Morphology of Potted 'UCR TP6-3', 'UCR 17-8', and Three CommercialBermudagrass Cultivars Greenhouse, Riverside, CA, 2019

| Cultivar | Leaf Blade Width (mm) | Leaf Blade Length (mm) | Internode Diameter (mm) | Internode Length (mm) |
|---|---|---|---|---|
| 'UCR TP6-3' | 1.50 a | 73.61 c | 0.90 a | 42.64 c |
| 'UCR 17-8' | 1.42 a | 61.31 b | 1.04 ab | 39.01 c |
| 'Bandera' | 1.97 b | 46.69 a | 1.23 c | 30.03 b |
| 'Tahoma 31' | 1.91 b | 50.22 a | 1.19 be | 24.25 a |
| 'TifTuf' | 2.04 b | 60.72 b | 1.11 be | 38.30 c |

Means followed by the same letter in a column are not significantly different at P = 0.05.

Morphological characteristics for mature plants of 'UCR TP6-3' grown in field plots in Riverside, Calif. are found in Table 2 alongside 'UCR 17-8' and four commercial cultivars 'Bandera', 'Santa Ana' (not patented), 'TifTuf', and 'Tifway' (not patented). Leaf blade width, leaf blade length, internode diameter, and internode length were measured. The field plots were established in a randomized complete block design with three replications in Riverside, Calif. in May 2017. Measurements were collected from three replications of each cultivar with 12 subsamples of each replication in 2019. 'UCR TP6-3's' leaf blade width was found to be similar to 'UCR 17-8', 'Tiftuf', and 'Tifway', but narrower than that of 'Bandera' and 'Santa Ana'. Leaf blade length of 'UCR TP6-3' was found to be similar to that of 'UCR 17-8', 'Bandera', 'Santa Ana', and 'Tiftuf', and shorter than that of 'Tifway'. 'UCR TP6-3's' internode diameter was similar to that of 'UCR 17-8', 'Tiftuf', and 'Tifway', and narrower than that of 'Bandera' and 'Santa Ana'. Internode length was similar to that of 'UCR 17-8' and 'Tiftuf', but longer than that of 'Bandera', 'Santa Ana', and 'Tifway'.

TABLE 2

Stolon Morphology of 'UCR TP6-3', 'UCR 17-8', and Four Commercial Bermudagrass Cultivars Field Plots, Riverside, CA, 2019

| Cultivar | Leaf Blade Width (mm) | Leaf Blade Length (mm) | Internode Diameter (mm) | Internode Length (mm) |
|---|---|---|---|---|
| 'UCR TP6-3' | 1.42 ab | 42.58 a | 1.01 a | 29.14 cd |
| 'UCR 17-8' | 1.39 ab | 45.13 a | 1.06 ab | 30.06 d |
| 'Bandera' | 1.85 d | 42.11 a | 1.32 c | 20.43 ab |

TABLE 2-continued

Stolon Morphology of 'UCR TP6-3', 'UCR 17-8', and Four Commercial Bermudagrass Cultivars Field Plots, Riverside, CA, 2019

| Cultivar | Leaf Blade Width (mm) | Leaf Blade Length (mm) | Internode Diameter (mm) | Internode Length (mm) |
|---|---|---|---|---|
| 'Santa Ana' | 1.63 c | 46.65 ab | 1.15 b | 17.69 a |
| 'TifTuf' | 1.36 a | 47.71 ab | 0.93 a | 24.04 bc |
| 'Tifway' | 1.52 bc | 52.80 b | 1.00 a | 23.50 b |

Means followed by the same letter in a column are not significantly different at P = 0.05.

A genetic screen was performed on a population of bermudagrass genotypes, which included 'UCR TP6-3', 'UCR 17-8', 'Bandera', 'Santa Ana', 'Tifway', 'Celebration' (also known as 'Riley's Super Sport', U.S. Plant Pat. No. 11,181), and 'Latitude 36' (U.S. Plant Pat. No. 24,271), using a genotype-by-sequencing platform called Diversity Arrays Technology sequencing (DArTseq). Results are found in Table 3. This genetic screen identified 6904 single nucleotide polymorphisms (SNP) that were found to be significantly informative when analyzing the genetic markers generated from the DArTseq data. Analysis of genetic markers was performed in R using the following packages: 'dartR', 'StAMPP', 'Rphylip', 'strataG', and 'ParallelStructure'. 'UCR TP6-3' was found to be closely related with 'UCR 17-8', with five markers differentiating between them, but distantly related to 'Bandera' (104 differentiating markers), 'Santa Ana' (126), 'Tifway' (56), 'Celebration' (282), and 'Latitude 36' (249). These numbers are indicative of genetic differences among the listed accessions, and indicate a quantifiable difference between 'UCR TP6-3' and current commercial cultivars.

TABLE 3

Number of Single Nucleotide Polymorphism (SNP) Markers Differentiating 'UCR TP6-3' From Other Bermudagrass Cultivars

| | Cultivar | | | | | | |
|---|---|---|---|---|---|---|---|
| Cultivar | 'UCR TP6-3' | 'UCR 17-8' | 'Bandera' | 'Santa Ana' | 'Tifway' | 'Celebration' | Latitude 36' |
| 'UCR TP6-3' | — | | | | | | |
| 'UCR 17-8' | 5 | — | | | | | |
| 'Bandera' | 104 | 109 | — | | | | |
| 'Santa Ana' | 126 | 131 | 26 | — | | | |
| 'Tifway' | 56 | 61 | 58 | 70 | — | | |
| 'Celebration' | 282 | 287 | 178 | 156 | 226 | — | |
| 'Latimde 36' | 249 | 253 | 144 | 122 | 192 | 34 | — |

Performance

'UCR TP 6-3' was advanced for further evaluation after several years of observations in the nursery and non-replicated test plots, based on good overall quality and performance under dry-down.

In 2017 replicated trials were performed in three locations: Thermal, Calif., Fairfax, Calif. and Riverside, Calif. Establishment (% ground cover), visual turfgrass quality in the summer and in the winter (1-9; 9=best), winter color retention (1-9; 9=highest), Normalized Difference Vegetation Index (NDVI, 0-1), Dark Green Color Index (DGCI, 0-0.666) using Digital Image Analysis (DIA), and seedhead production (1-9; 1=no seedheads) were evaluated from 2017 to 2019. Comparison of 'UCR TP6-3' with commercial cultivars ('Bandera', 'Santa Ana', 'TifTuf', 'Tifway') and 'UCR 17-8' is presented in Tables 4, 5, and 6. In Riverside, Calif., 'UCR TP6-3' had the highest summer and winter quality. In northern California (Fairfax, Calif.), summer quality of 'UCR TP6-3' was comparable to other cultivars and 'UCR 17-8', slightly lower than 'Tifway' and higher than 'Santa Ana'. In the desert (Thermal, Calif.), 'UCR TP6-3' was among the best performing entries both in the summer and winter. In the summer its quality was lower than 'TifTuf', but higher than 'Bandera', while in the winter it was slightly lower than 'UCR 17-8' and significantly higher than 'Bandera' and 'Santa Ana'. Winter color retention of 'UCR TP6-3' was good in all three locations. In Thermal, Calif., it retained color better than 'Santa Ana' and 'Bandera'. In Fairfax, Calif., differences among entries were less pronounced. Winter color retention of 'UCR TP6-3' was lower than 'TifTuf', but comparable to 'UCR 17-8', 'Bandera' and 'Santa Ana', and higher than 'Tifway'. Seedhead production of 'UCR TP6-3' varied across the locations. At all locations seedhead production was higher than that of 'Tifway'. In Riverside, Calif., it was lower than 'TifTuf' and higher than 'UCR 17-8', while in Thermal, Calif. it was comparable to 'TifTuf' and lower than 'Santa Ana' and 'UCR 17-8'. In Fairfax, Calif., seedhead production of 'UCR TP6-3' was significantly lower than 'TifTuf'.

TABLE 4

Thermal, CA 2017-2019

| | Turfgrass Quality | | Winter Color |
|---|---|---|---|
| Cultivar | S | W | Retention |
| 'UCRTP6-3' | 6.1 ab | 5.8 ab | 6.8 ab |
| 'UCR 17-8' | 6.0 b | 6.3 a | 7.2 a |
| 'Bandera' | 5.4 c | 4.9 cd | 6.2 b |
| 'Santa Ana' | 6.1 ab | 4.5 d | 5.2 c |
| 'TifTuf' | 6.5 a | 5.2 bcd | 6.7 ab |
| 'Tifway' | 5.9 b | 5.3 bc | 6.9 ab |
| Significance | *** | *** | *** |

| | NDVI | | DGCI | | Seedhead | Establishment (8 |
|---|---|---|---|---|---|---|
| Cultivar | S | W | S | W | Production | WAP) |
| 'UCRTP6-3' | 0.70 a | 0.65 a | 0.46 a | 0.44 a | 2.7 ab | 88.0 ab |
| 'UCR 17-8' | 0.69 a | 0.68 a | 0.45 a | 0.45 a | 3.7 b | 94.1 ab |
| 'Bandera' | 0.65 a | 0.62 a | 0.44 a | 0.44 a | 2.5 ab | 98.0 a |
| 'Santa Ana' | 0.68 a | 0.61 a | 0.45 a | 0.41 a | 3.7 b | 86.4 ab |
| 'TifTuf' | 0.69 a | 0.62 a | 0.44 a | 0.43 a | 3.0 ab | 96.5 ab |
| 'Tifway' | 0.66 a | 0.64 a | 0.44 a | 0.44 a | 1.7a | 68.6 b |
| Significance | ~ | ~ | | | *** | * |

Means followed by the same letter in a column are not significantly different at P = 0.05
Significance levels: *P < 0.001, P < 0.01, *P < 0.05, ~P < 0.1. S = Summer, W = Winter.

TABLE 5

Fairfax, CA 2017-2019

| | Turfgrass Quality | | Winter Color | NDVI | |
|---|---|---|---|---|---|
| Cultivar | S | W | Retention | S | W |
| 'UCR TP6-3' | 5.9 abc | 3.9 a | 4.3 ab | 0.72 a | 0.56 ab |
| 'UCR 17-8' | 6.0 ab | 3.9 a | 3.8 ab | 0.72 a | 0.57 ab |
| 'Bandera' | 5.6 bc | 4.1 a | 4.3 ab | 0.69 ab | 0.58 a |

TABLE 5-continued

| Fairfax, CA 2017-2019 | | | | | |
|---|---|---|---|---|---|
| 'Santa Ana' | 5.3 c | 4.0 a | 4.3 ab | 0.64 b | 0.50 b |
| 'TifTuf' | 5.9 abc | 4.4 a | 4.9 a | 0.71 a | 0.56 ab |
| 'Tifway' | 6.4 a | 3.4 a | 3.3 b | 0.73 a | 0.55 ab |
| Significance | *** | | ~ | *** | * |

| | DGCI | | Seedhead | Establishment (8 |
|---|---|---|---|---|
| Cultivar | S | W | Production | WAP) |
| 'UCR TP6-3' | 0.38 a | 0.41 a | 3.1 a | 27.3 a |
| 'UCR 17-8' | 0.38 a | 0.41 a | 2.9 a | 44.7 a |
| 'Bandera' | 0.38 a | 0.41 a | 2.4 a | 38.2 a |
| 'Santa Ana' | 0.37 a | 0.40 a | 3.1 a | 24.8 a |
| 'TifTuf' | 0.37 a | 0.39 a | 4.7 b | 39.3 a |
| 'Tifway' | 0.38 a | 0.39 a | 2.7 a | 16.0 a |
| Significance | | | *** | |

Means followed by the same letter in a column are not significantly different at P = 0.05. Significance levels: *P < 0.001, P < 0.01, *P < 0.05, ~P < 0.1. S = Summer, W

TABLE 6

| Riverside, CA 2017-2019 | | | | | |
|---|---|---|---|---|---|
| | Turfgrass Quality | | Winter Color | NDVI | |
| Cultivar | S | W | Retention | S | W |
| 'UCRTP6-3' | 6.7 a | 5.8 a | 6.9 a | 0.73 a | 0.62 a |
| 'UCR 17-8' | 6.3 b | 5.5 a | 6.3 ab | 0.72 ab | 0.58 ab |
| 'Bandera' | 5.7 c | 4.6 c | 5.4 bc | 0.67 c | 0.51 cd |
| 'Santa Ana' | 6.4 ab | 4.7 bc | 4.9 c | 0.71 abc | 0.47 d |
| 'TifTuf' | 6.3 b | 5.6 a | 6.7 a | 0.69 bc | 0.59 ab |
| 'Tifway' | 6.2 b | 5.3 ab | 6.6 a | 0.69 bc | 0.55 bc |
| Significance | *** | *** | *** | *** | *** |

| | DGCI | | Seedhead | Establishment (8 |
|---|---|---|---|---|
| Cultivar | S | W | Production | WAP) |
| 'UCRTP6-3' | 0.47 a | 0.42 a | 3.3 ab | 96.8 a |
| 'UCR 17-8' | 0.47 a | 0.43 a | 1.6 a | 66.5 a |
| 'Bandera' | 0.45 ab | 0.41 a | 3.0 ab | 65.1 a |
| 'Santa Ana' | 0.46 ab | 0.36 b | 2.7 ab | 91.9 a |
| 'TifTuf' | 0.45 b | 0.41 a | 3.9 b | 83.3 a |
| 'Tifway' | 0.45 ab | 0.41 a | 1.7 a | 74.1 a |
| Significance | ** | *** | ** | |

Means followed by the same letter in a column are not significantly different at P = 0.05. Significance levels: * P < 0.001, P < 0.01, *P < 0.05, ~P < 0.1. S = Summer, W = Winter.

To evaluate performance under regular fairway management in Northern California a study was started in Napa, Calif. in 2019. Plots were established using sod and placed in two fairways. Turfgrass quality in the summer and in the winter (1-9; 9=best), winter color retention (1-9; 9=highest), NDVI (0-1), density (1-9; 9=highest), uniformity (1-9; 9=most uniform) and seedhead production (1-9; 1=no seedheads) were evaluated from 2019 to 2022. Performance of 'UCR TP6-3' in comparison to commercial bermudagrass cultivars and 'UCR 17-8' is shown in Table 7. 'UCR TP6-3' showed good quality both in the summer and in the winter. In the summer, quality of 'UCR TP6-3' was comparable to 'Latitude 36', lower than 'UCR 17-8' and higher than other cultivars. In the winter, its quality was similar to 'UCR 17-8', 'Latitude 36', 'TifTuf', 'Santa Ana', 'Bandera' and 'Tifway II' (not patented), and higher than 'Celebration' and 'Tahoma 31'. Winter color retention of 'UCR TP6-3' was higher than of 'Celebration' and 'Tahoma 31', slightly lower than 'Santa Ana' and 'TifTuf', and similar to 'UCR 17-8', 'Bandera' and 'Latitude 36'. Genetic color of 'UCR TP6-3' was dark, similar to 'Bandera', 'Tahoma 31', 'UCR 17-8' and 'Latitude 36'. Density of 'UCR TP6-3' was good, comparable to 'Bandera', 'Latitude 36', 'Santa Ana', 'TifTuf' and 'Tifway II' and higher than 'Celebration'. Uniformity was lower than 'UCR 17-8', but higher than 'Celebration'. Seedhead production was moderate.

TABLE 7

| Fairway Trial, Napa, CA 2019-2022 | | | | | |
|---|---|---|---|---|---|
| | Turfgrass Quality | | Winter Color | Genetic | NDVI |
| Cultivar | S | W | Retention | Color | S |
| 'UCRTP6-3' | 7.0 ab | 5.3 a | 5.9 ab | 8.2 ab | 0.76 a |
| 'UCR 17-8' | 7.8 a | 5.4 a | 5.9 ab | 8.3 a | 0.76 a |
| 'Bandera' | 6.7 bcd | 4.6 ab | 5.2 ab | 8.5 a | 0.73 a |
| 'Celebration' | 4.5 f | 3.2 c | 2.7 d | 6.5 c | 0.66 b |
| 'Latitude 36' | 7.4 ab | 5.2 a | 5.2 ab | 8.2 ab | 0.73 a |
| 'Santa Ana' | 6.7 bc | 5.7 a | 6.3 a | 7.7 abc | 0.75 a |
| 'Tahoma 31' | 5.8 de | 3.9 bc | 3.7 cd | 8.5 a | 0.70 ab |
| 'TifTuf' | 6.0 cde | 5.6 a | 6.3 a | 6.7 bc | 0.72 ab |
| 'Tifway II' | 5.8 e | 4.9 ab | 4.8 bc | 7.5 abc | 0.70 ab |
| Significance | *** | *** | *** | *** | *** |

| | NDVI | | | Seedhead |
|---|---|---|---|---|
| Cultivar | W | Density | Uniformity | Prod. |
| 'UCRTP6-3' | 0.58 ab | 7.6 ab | 6.8 abcd | 4.4 ab |
| 'UCR 17-8' | 0.57 ab | 8.1 a | 7.8 a | 3.1 a |
| 'Bandera' | 0.54 abc | 7.7 ab | 6.9 abcd | 3.6 ab |
| 'Celebration' | 0.41 d | 5.2 c | 5.4 e | 5.3 ab |
| 'Latitude 36' | 0.51 abc | 7.6 ab | 7.4 ab | 3.0 a |
| 'Santa Ana' | 0.60 a | 7.7 ab | 7.2 abc | 5.9 b |
| 'Tahoma 31' | 0.45 cd | 6.7 b | 5.8 de | 2.9 a |
| 'TifTuf' | 0.57 ab | 7.4 ab | 6.3 bcde | 5.6 ab |
| 'Tifway II' | 0.50 bcd | 7.1 ab | 6.1 cde | 5.9 b |
| Significance | *** | * * * | ** | *** |

Means followed by the same letter in a column are not significantly different at P = 0.05. Significance levels *P < 0.001, P < 0.01, *P < 0.05, ~P < 0.1. S = Summer, W = Winter.

'UCR TP6-3' was added as local check to the 2019 National Turfgrass Evaluation Program ("NTEP") National Bermudagrass Test in Riverside, Calif. Commercial checks in this study were 'Astro' (not patented), 'Latitude 36', 'Tahoma 31', 'TifTuf' and 'Tifway'. The study was planted in June and early July 2019 and was mowed to ⅝ in. Establishment rate (% ground cover), turfgrass quality (1-9; 9=best), spring greenup (1-9; 1=dormant), leaf texture (1-9; 9=finest), genetic color (1-9; 9=darkest green), and fall/winter color retention (1-9; 9=highest; starting second full year of the trial) were evaluated. After full establishment was reached, deficit irrigation was applied in the summer of each year (July/August to October) at 35% $ET_0$. During this period turfgrass quality and percent green retention were also evaluated. Data comparing 'UCR TP6-3' with commercial bermudagrass cultivars and 'UCR 17-8' are presented in Table 8. 'UCR TP6-3' had good quality under regular irrigation, similar to 'UCR 17-8' and 'TifTuf', and higher than 'Astro', 'Latitude 36', 'Tahoma 31' and 'Tifway'. Under 35% $ET_0$ 'UCR TP6-3' retained quality similar to 'Tahoma 31', lower than 'TifTuf' and 'UCR 17-8', and higher 'Latitude 36' and 'Tifway'. Green cover of 'UCR TP6-3' retained at the end of reduced irrigation period was lower than 'TifTuf' and higher than 'Latitude 36' and 'Tifway'. Winter color retention of 'UCR TP6-3' was very good, comparable to 'TifTuf' and 'UCR 17-8', and higher than other cultivars. Spring green-up was also similar to 'TifTuf' and 'UCR 17-8'. Genetic color was lighter than 'Tahoma 31', similar to 'UCR 17-8' and 'Tifway'. 'UCR TP6-3' had relatively fine texture, similar to 'Latitude 36' and 'UCR 17-8'.

TABLE 8

2019 NTEP National Bermudagrass Test
Riverside, CA

| Cultivar | Turfgrass Quality R | Turfgrass Quality D | Green Cover - Deficit Irrigation | Fall/ Winter Color Reten-tion | Spring Green-Up | Gen-etic Color | Leaf Tex-ture |
|---|---|---|---|---|---|---|---|
| 'UCRTP6-3' | 6 0 a | 5.3 ab | 53.8 abc | 7 1 a | 7.1 a | 7.3 ab | 7.0 a |
| UCR 17-8' | 6.0 a | 5.8 a | 58.5 ab | 7.1 a | 7.1 a | 7.5 ab | 7.0 a |
| 'Astro' | 4.3 c | 4.2 bc | 30.3 abc | 4 6 c | 5.0 b | 4.3 c | 5.8 b |
| 'Latitude 36' | 4.6 bc | 2.8 c | 17.0 c | 4.7 c | 5.9 ab | 6.2 b | 6.8 a |
| 'Tahoma 31' | 4.8 bc | 4.7 ab | 39.0 abc | 3.2 d | 6.3 ab | 8.2 a | 6.7 ab |
| 'TifTuf' | 6.6 a | 5.7 a | 69.2 a | 7.2 a | 6.9 a | 6.0 b | 6.7 ab |
| 'Tifway' | 5.1 b | 4.2 bc | 25.4 bc | 5.7 b | 6.2 ab | 6.7 ab | 6.5 ab |
| Significance | *** | *** | ** | * * * | ** | *** | ** |

Means followed by the same letter in a column are not significantly different at P=0.05
Significance levels: *P < 0.001, P < 0.01, *P < 0.05, ~P < 0.1. R = Regular Irrigation; D = Deficit Irrigation.

'UCR TP6-3' was tested for prolonged drought tolerance in a field trial in Riverside, Calif., for two years (2020 & 2021) from June to November. Each year, prolonged drought conditions were simulated using two subsequent dry-down periods (60 days; irrigation withheld) followed by recovery periods (14 days; irrigation provided). Plants were evaluated on their performance using measurements of percent living (green) coverage (PC), normalized difference vegetative index (NDVI, 0-1), and overall turf quality (scale of 1 to 9, 9=best). Percent green (living) coverage (PC) was measured on eight separate events per year with digital image analysis using the image processing software ImageJ. Results are presented in Table 9 and Table 10. During the first experimental year, 'UCR TP6-3' was found to exhibit a similar mean PC to 'UCR 17-8', 'Bandera', 'Celebration', 'Santa Ana', 'TifTuf', and 'Tifway II' on all eight events. During the second experimental year, 'UCR TP6-3' was found to exhibit a similar mean PC to 'UCR 17-8', 'Bandera', 'Santa Ana', 'TifTuf', and 'Tifway II' on all eight events; but a lower mean PC than 'Celebration' on two events. NDVI was used as a metric to measure overall plant health using a handheld Green Seeker. Increase of cover observed in second cycle of 2021 resulted from significant rain event (0.2 in).

TABLE 9

Green Cover (%) After 20, 40, and 60 Days
Without Irrigation in Riverside, CA

| Cultivar | Drydown Cycle I 20 d | Drydown Cycle I 40 d | Drydown Cycle I 60 d | Recovery Period 1 |
|---|---|---|---|---|
| 2020 | | | | |
| 'UCRTP6-3' | 92.4 a | 65.8 a | 30.4 a | 100.0 a |
| 'UCR 17-8' | 96.5 a | 74.8 a | 39.9 a | 100.0 a |

TABLE 9-continued

Green Cover (%) After 20, 40, and 60 Days
Without Irrigation in Riverside, CA

| | | | | |
|---|---|---|---|---|
| 'Bandera' | 72.6 a | 55.2 a | 38.8 a | 100.0 a |
| 'Celebration' | 100.0 a | 100.0 a | 64.8 a | 100.0 a |
| 'Santa Ana' | 98.8 a | 69.0 a | 42.7 a | 100.0 a |
| 'TifTuf' | 98.1 a | 84.5 a | 39.1 a | 100.0 a |
| 'Tifway II' | 85.4 a | 51.6 a | 22.0 a | 96.4 a |
| 2021 | | | | |
| 'UCRTP6-3' | 66.5 a | 36.4 a | 5.3 b | 67.6 a |
| 'UCR 17-8' | 70.2 a | 28.9 a | 3.2 b | 52.2 a |
| 'Bandera' | 41.3 a | 21.8 a | 3.6 b | 45.0 a |
| 'Celebration' | 73.7 a | 66.3 a | 30.6 a | 74.0 a |
| 'Santa Ana' | 64.4 a | 37.6 a | 13.8 ab | 60.3 a |
| 'TifTuf' | 74.9 a | 49.5 a | 13.0 ab | 77.6 a |
| 'Tifway II' | 30.6 a | 11.3 a | 3.0 b | 68.7 a |

| Cultivar | Drydown Cycle II 20 d | Drydown Cycle II 40 d | Drydown Cycle II 60 d | Recovery Period II |
|---|---|---|---|---|
| 2020 | | | | |
| 'UCRTP6-3' | 72.2 ab | 37.2 ab | 32.0 ab | 71.3 ab |
| 'UCR 17-8' | 69.0 ab | 31.1 ab | 23.6 ab | 77.8 ab |
| 'Bandera' | 52.3 ab | 25.7 ab | 19.6 ab | 52.4 b |
| 'Celebration' | 92.1 ab | 64.2 ab | 58.8 ab | 75.9 ab |
| 'Santa Ana' | 50.4 ab | 25.2 ab | 27.9 ab | 65.0 ab |
| 'TifTuf' | 100.0 a | 80.2 a | 70.7 a | 100.0 a |
| 'Tifway II' | 44.3 b | 15.4 b | 9.1 b | 44.3 b |
| 2021 | | | | |
| 'UCRTP6-3' | 18.5 bc | 13.1 ab | 22.6 ab | 29.8 ab |
| 'UCR 17-8' | 9.4 bc | 6.6 b | 8.9 ab | 12.2 ab |
| 'Bandera' | 6.8 bc | 5.4 b | 5.6 b | 6.3 b |
| 'Celebration' | 50.9 a | 35.0 ab | 49.8 a | 55.2 a |
| 'Santa Ana' | 22.3 abc | 15.8 ab | 20.1 ab | 26.7 ab |
| 'TifTuf' | 37.1 ab | 21.9 ab | 36.0 ab | 48.5 ab |
| 'Tifway II' | 6.1 c | 4.9 b | 5.4 b | 8.2 b |

Means followed by the same letter in a column are not significantly different at P = 0.05.

TABLE 10

Normalized Difference Vegetation Index (NDVT, 0-1) After
20, 40, and 60 Days Without Irrigation in Riverside, CA

| Cultivar | Drydown Cycle 1 20 d | Drydown Cycle 1 40 d | Drydown Cycle 1 60 d | Recovery Period 1 |
|---|---|---|---|---|
| 2020 | | | | |
| 'UCRTP6-3' | 0.64 a | 0.51 a | 0.36 a | 0.81 a |
| UCR 17-8' | 0.63 a | 0.51 a | 0.36 a | 0.75 a |
| 'Bandera' | 0.53 a | 0.44 a | 0.35 a | 0.65 a |
| 'Celebration' | 0.67 a | 0.56 a | 0.43 a | 0.74 a |
| 'Santa Ana' | 0.63 a | 0.49 a | 0.38 a | 0.65 a |
| 'TifTuf | 0.59 a | 0.47 a | 0.34 a | 0.80 a |
| Tifway II | 0.53 a | 0.41 a | 0.28 a | 0.64 a |
| 2021 | | | | |
| 'UCRTP6-3' | 0.50 a | 0.34 a | 0.27 ab | 0.46 a |
| UCR 17-8' | 0.55 a | 0.32 a | 0.23 ab | 0.36 a |
| 'Bandera' | 0.40 a | 0.27 a | 0.23 ab | 0.32 a |
| 'Celebration' | 0.52 a | 0.44 a | 0.39 a | 0.50 a |
| 'Santa Ana' | 0.51 a | 0.36 a | 0.31 ab | 0.43 a |
| 'TifTuf | 0.54 a | 0.41 a | 0.35 ab | 0.55 a |
| 'Tifway IT | 0.36 a | 0.22 a | 0.20 b | 0.38 a |

TABLE 10-continued

Normalized Difference Vegetation Index (NDVT, 0-1) After 20, 40, and 60 Days Without Irrigation in Riverside, CA

| | Drydown Cycle II | | | Recovery |
|---|---|---|---|---|
| Cultivar | 20 d | 40 d | 60 d | Period II |
| | | 2020 | | |
| 'UCRTP6-3' | 0.48 a | 0.40 a | 0.39 a | 0.49 a |
| UCR 17-8' | 0.44 a | 0.37 a | 0.35 a | 0.47 a |
| 'Bandera' | 0.36 a | 0.32 a | 0.31 a | 0.35 a |
| 'Celebration' | 0.50 a | 0.45 a | 0.43 a | 0.47 a |
| 'Santa Ana' | 0.37 a | 0.33 a | 0.32 a | 0.45 a |
| 'TifTuf | 0.55 a | 0.46 a | 0.43 a | 0.57 a |
| Tifway II | 0.36 a | 0.27 a | 0.25 a | 0.36 a |
| | | 2021 | | |
| 'UCRTP6-3' | 0.32 abc | 0.25 ab | 0.24 ab | 0.24 a |
| UCR 17-8' | 0.26 ab | 0.20 b | 0.20 ab | 0.19a |
| 'Bandera' | 0.24 c | 0.20 ab | 0.17 ab | 0.15 a |
| 'Celebration' | 0.40 a | 0.33 a | 0.32 a | 0.34 a |
| 'Santa Ana' | 0.28 abc | 0.27 ab | 0.23 ab | 0.27 a |
| 'TifTuf | 0.39 ab | 0.31 ab | 0.25 ab | 0.30 a |
| Tifway II | 0.22 c | 0.18 b | 0.16b | 0.18 a |

Means followed by the same letter in a column are not significantly different at P = 0.05.

When compared to other commercially available bermudagrass cultivars 'UCR TP6-3' possesses as good or better winter color retention. Overall turf quality characteristics of 'UCR TP6-3' are similar to or better than the latest bermudagrass cultivar releases. 'UCR TP6-3' and 'UCR 17-8' are genetically similar, sharing the same accessions used in crossing. 'UCR 17-8' is superior in terms of drought resistance, whereas the 'UCR TP6-3' possesses slightly better aesthetic turf quality characteristics. Other differences between the two include a slightly higher seedhead production in 'UCR TP6-3' compared to 'UCR 17-8' in Riverside and Northern California, however lower in the desert. 'UCR TP6-3' has better performance and quicker recovery than 'UCR 17-8' when no irrigation is applied, however 'UCR 17-8' has better performance under reduced irrigation (35% ET replacement). 'UCR 17-8' also has more uniform performance in various locations across California.

I claim:

1. A new and distinct Bermudagrass plant named 'UCR TP6-3', substantially as described and illustrated herein.

* * * * *